United States Patent
Alt et al.

(10) Patent No.: US 8,124,776 B2
(45) Date of Patent: Feb. 28, 2012

(54) PROCESS AND INTERMEDIATES FOR PREPARING ARZOXIFENE

(75) Inventors: Charles Arthur Alt, Greenwood, IN (US); Douglas Patton Kjell, West Lafayette, IN (US); Tony Yantao Zhang, Shanghai (CN); Fu-Yao Zhang, Carmel, IN (US); Jared Wade Fennell, New Ross, IN (US); Kevin Dale Seibert, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 288 days.

(21) Appl. No.: 12/526,657

(22) PCT Filed: Mar. 3, 2008

(86) PCT No.: PCT/US2008/055626
§ 371 (c)(1),
(2), (4) Date: Aug. 11, 2009

(87) PCT Pub. No.: WO2008/115686
PCT Pub. Date: Sep. 25, 2008

(65) Prior Publication Data
US 2010/0137602 A1 Jun. 3, 2010

Related U.S. Application Data

(60) Provisional application No. 60/895,154, filed on Mar. 16, 2007.

(51) Int. Cl.
*C07D 409/00* (2006.01)
*A61K 31/445* (2006.01)

(52) U.S. Cl. .................................. 546/202; 514/320
(58) Field of Classification Search .................. 546/202; 514/320
See application file for complete search history.

(56) References Cited

U.S. PATENT DOCUMENTS
6,077,852 A 6/2000 Bales et al.

FOREIGN PATENT DOCUMENTS
EP 0 729 956 A 9/1996

*Primary Examiner* — Janet Andres
*Assistant Examiner* — John Mabry
(74) *Attorney, Agent, or Firm* — MaCharri Vorndran-Jones

(57) ABSTRACT

The present invention provides for novel compounds of formula I wherein X is S or S(O); $R^1$ and $R^2$ are each independently selected from the group consisting of —$CH_2CH_3$ and phenyl; or $R^1$ and $R^2$ combine to form morpholino; and processes to prepare arzoxifene.

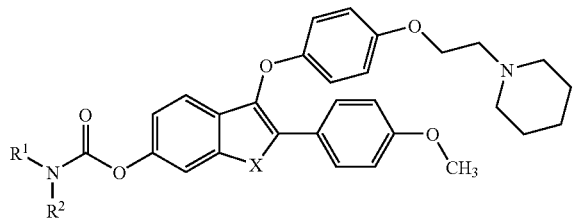

(I)

16 Claims, No Drawings

PROCESS AND INTERMEDIATES FOR PREPARING ARZOXIFENE

This application is a United States national phase entry, pursuant to 35 U.S.C. 371, of PCT/US2008/055626, filed on 3 Mar. 2008, which claims the benefit of U.S. provisional patent application Ser. No. 60/895,154, filed 16 Mar. 2007, and hereby incorporated by reference in their entirety.

The present invention relates to a process and intermediates for the preparation of 2-(4-methoxyphenyl)-3-[4-[2-(1-piperidinyl)ethoxy]phenyoxy]benzo[b]thiophene-6-ol. The compound 2-(4-methoxyphenyl)-3-[4-[2-(1-piperidinyl)ethoxy]phenyoxy]benzo[b]thiophene-6-ol is also known as arzoxifene (hereinafter "arzoxifene").

The compound arzoxifene, methods of preparing arzoxifene, as well as pharmaceutical formulations containing arzoxifene, are described in U.S. Pat. No. 5,723,474 (herein "'474 patent"). The methods for preparing arzoxifene, as described in the '474 patent, use methylene chloride. Methylene chloride is considered to be a potential occupational carcinogen by the United States Occupational Safety and Health Administration (OSHA). The use of methylene chloride is ecologically and commercially undesirable. In the synthesis of arzoxifene, a benzyl protecting group is used to direct the bromination to the correct site and to prevent impurities during the step in which the side chain is installed. Removal of the benzyl protecting group to yield arzoxifene requires multiple charges of palladium catalyst, a heavy metal. Thus, there is a need for a protecting group that is used to direct the bromination at the desired position, to prevent impurities, and does not require multiple charges of catalyst for its removal. There is also a need for a safer, more ecologically prudent, and commercially feasible process to consistently produce arzoxifene of high purity and consistent pharmaceutical quality. It is particularly desired that the process yield a crystalline form of arzoxifene HCl as described in U.S. Pat. Nos. 6,610,706 and 7,122,203 and WO200234741.

The present invention provides novel intermediates for the use in the synthesis of arzoxifene. The present invention provides an improved process and intermediates that eliminates the requirement for methylene chloride as a processing solvent, significantly reduces the amount of palladium catalyst required, provides a commercially feasible method for consistently preparing arzoxifene of pharmaceutically acceptable quality, and can be used to prepare crystalline Form III or Form V arzoxifene.

The present invention provides novel compounds of the formula:

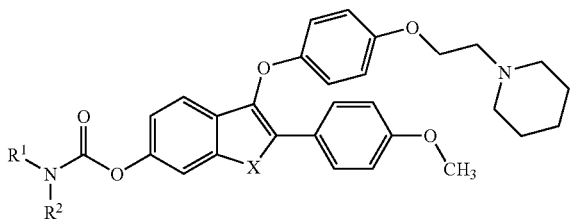

wherein
X is S or S(O);
$R^1$ and $R^2$ are each independently selected from the group consisting of —$CH_2CH_3$ and phenyl; or $R^1$ and $R^2$ combine to form morpholino.

The invention provides compounds of formula I:

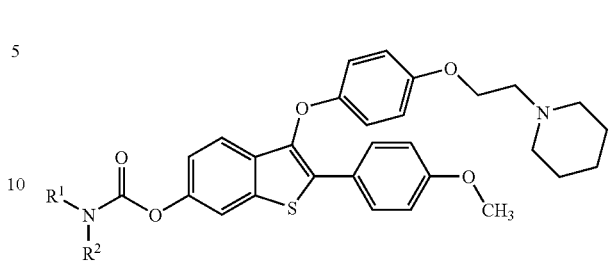

wherein
$R^1$ and $R^2$ are each independently —$CH_2CH_3$, phenyl; or $R^1$ and $R^2$ combine to form morpholino; and compounds of formula II:

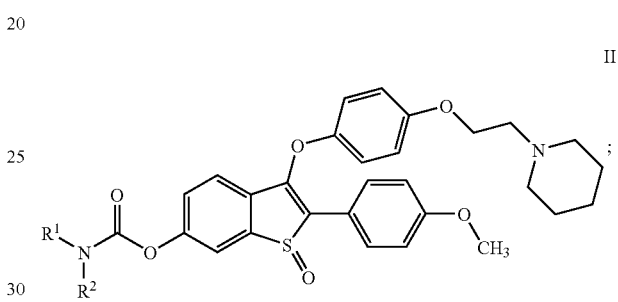

wherein $R^1$ and $R^2$ are defined as above.

The invention further provides a process for preparing arzoxifene: comprising
a) reducing the sulfoxide of a compound of Formula II to form a compound of Formula I; and
b) deprotecting a compound of Formula I to form arzoxifene.

The invention provides a process for preparing arzoxifene in the free base form.

The invention further provides a process wherein the hydrochloride salt of arzoxifene is formed.

The invention further provides a process wherein the arzoxifene is prepared as Form III.

The invention further provides a process wherein the arzoxifene is prepared as Form V.

The preferred substituent for each $R^1$ and $R^2$ is —$CH_2CH_3$. A preferred embodiment is when X is S and each $R^1$ and $R^2$ is —$CH_2CH_3$. A further preferred embodiment is when X is S(O) and each $R^1$ and $R^2$ is —$CH_2CH_3$.

The terms and abbreviations used in the instant Schemes, Preparations, Examples and Procedures have their normal meanings unless otherwise designated. For example, as used herein, the following terms have the meanings indicated: "THF" refers to tetrahydrofuran, "$Et_3N$" refers to triethylamine, "DMAP" refers to N,N-Dimethyl-4-Pyridinamine, "EtOAc" refers to ethyl acetate, "AcOH" refers to acetic acid, "NBS" refers to N-bromosuccinimide, "DMF" refers to dimethylformamide, "IPrOH" refers to isopropyl alcohol, "Pd/C" refers to palladium on carbon, "ESI" refers to mass spectrometry-electrospray ionization, and "morpholino" refers to a morpholine or 1-oxa-4-azacyclohexane substituent. Besides arzoxifene, the preparations and examples are named using AutoNom 2000 in ISIS/Draw Version 2.5 SP1.

As used herein the term "arzoxifene" means a compound having the structure:

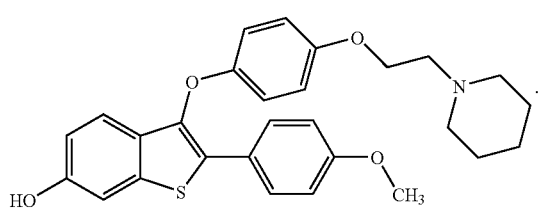

Seed crystals are obtained by synthesizing the compound by the described procedure without seeding. Compounds and processes of this invention wherein $R^1$ and $R^2$ are each —$CH_2CH_3$ are especially preferred because the protecting groups are easily removed and significantly reduce the amount of catalyst required for the process.

Scheme I

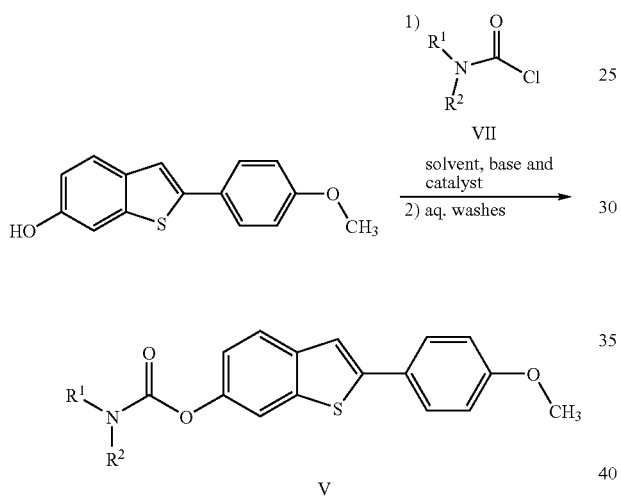

Scheme I describes the first step in the synthesis where the 6-OH of 2-(4-methoxy-phenyl)-benzo[b]thiophen-6-ol is protected. Here, 2-(4-methoxy-phenyl)-benzo[b]thiophen-6-ol reacts with an N,N disubstituted carbamyl chloride (compound of formula VII) in a solvent, a base, and a catalyst to form the compound of formula V. For the compound of formula VII, $R^1$ and $R^2$ can independently be —$CH_2CH_3$ or phenyl or $R^1$ and $R^2$ combine to form morpholino. Preferably, $R^1$ and $R^2$ are each —$CH_2CH_3$. Preferably, the solvent is THF, the base is triethylamine, and the catalyst is DMAP.

Scheme II

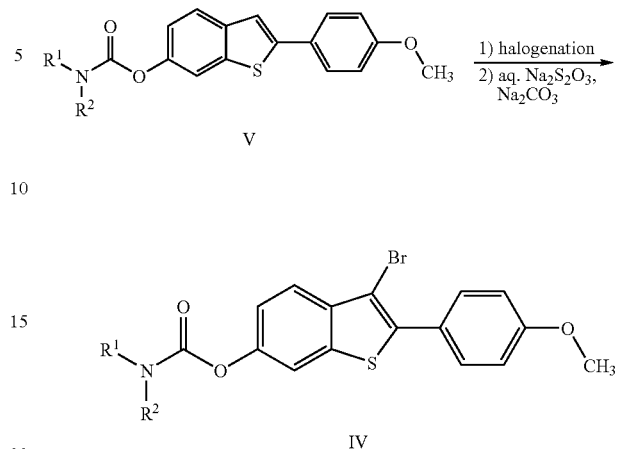

Scheme II shows the compound of formula V undergoing halogenation to form the compound of formula IV. Preferably, the halogenation is performed using NBS.

Scheme III

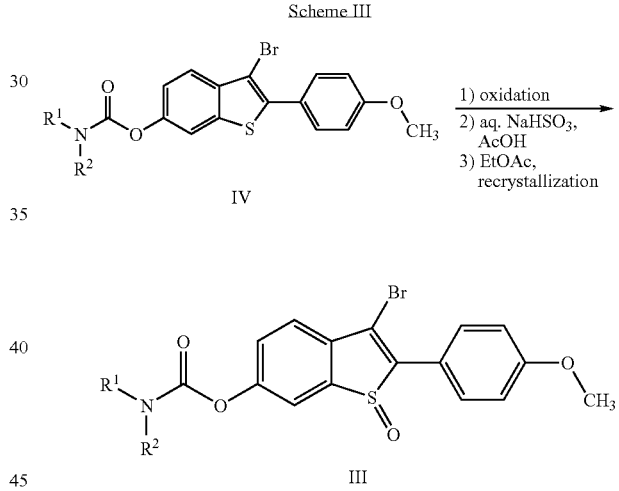

Scheme III shows the oxidation of the sulfur in the benzothiophene ring to the sulfinyl of compound III. Preferably, the oxidation is performed in the presence of $H_2O_2$, $H_2SO_4$, and sulfolane.

Scheme IV

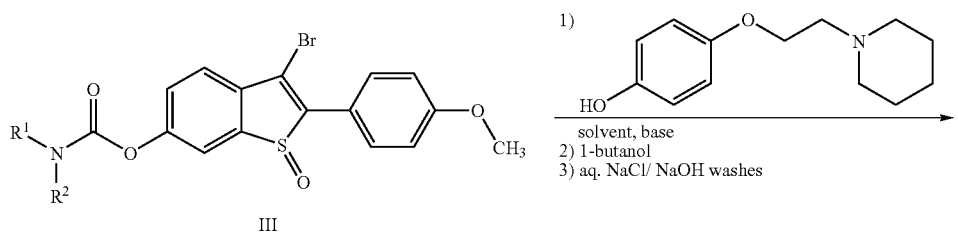

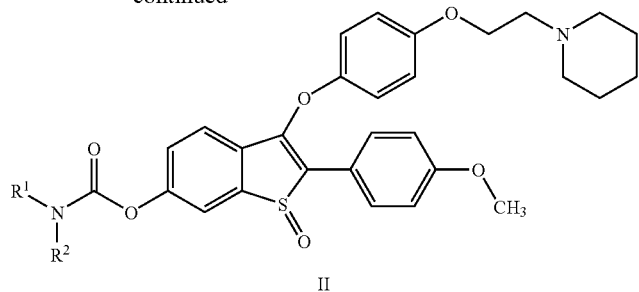

II

Scheme IV shows the coupling of 4-(2-piperidin-1-yl-ethoxy)-phenol to the compound of formula III in the presence of a solvent and a base to form the compound of formula II. Preferably, the solvent is DMF and the base is potassium t-butoxide.

Scheme V

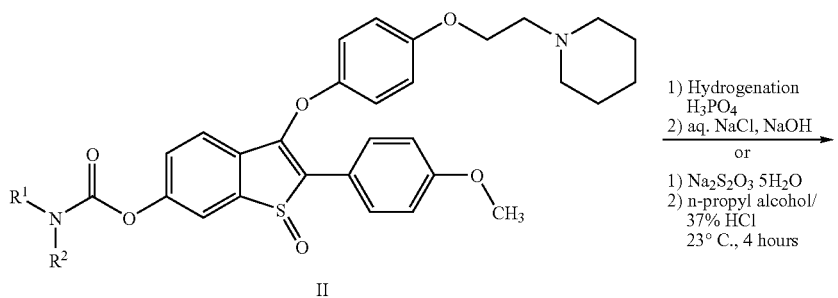

1) Hydrogenation H$_3$PO$_4$
2) aq. NaCl, NaOH or

1) Na$_2$S$_2$O$_3$ 5H$_2$O
2) n-propyl alcohol/ 37% HCl 23° C., 4 hours

II

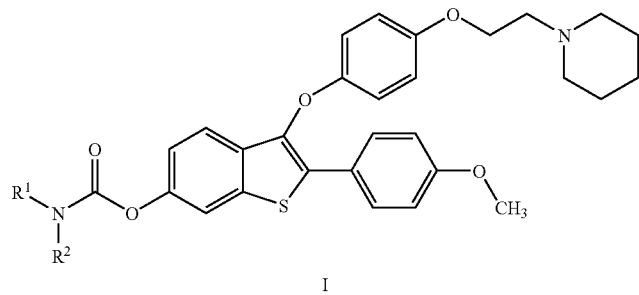

I

In Scheme V, the sulfinyl in the compound of formula II is reduced to the sulfur in the compound of formula I. The sulfinyl can be reduced by hydrogenation using H$_2$ and using Pd/C as the catalyst or by using Na$_2$S$_2$O$_3$.

Scheme VI

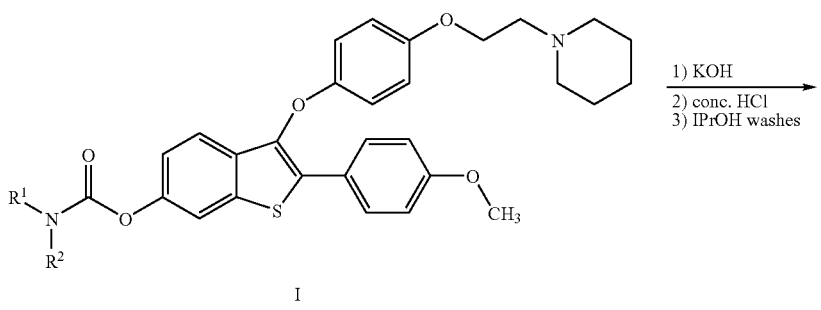

1) KOH
2) conc. HCl
3) IPrOH washes

I

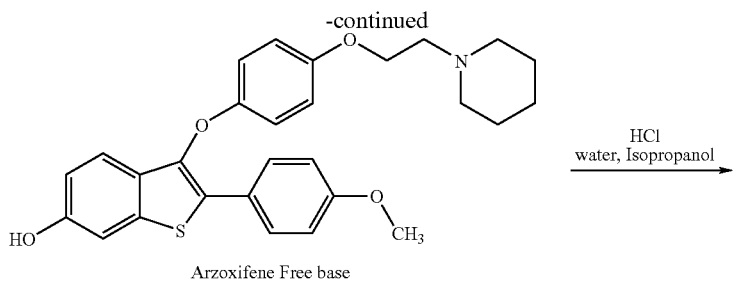

Arzoxifene Free base

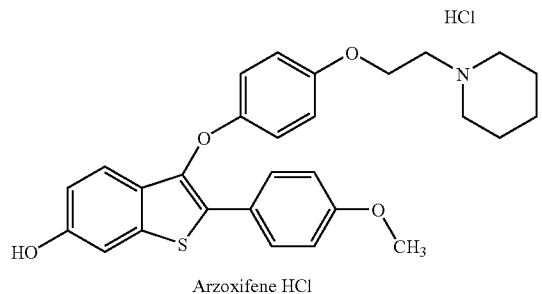

Arzoxifene HCl

In Scheme VI, a compound of formula I is deprotected to afford arzoxifene in the free base form which is then converted to arzoxifene HCl.

PREPARATION 1

Diethyl-carbamic acid 2-(4-methoxy-phenyl)-benzo[b]thiophen-6-yl ester

Combine 2-(4-methoxy-phenyl)-benzo[b]thiophen-6-ol (10.00 g, 39.01 mmoles), DMAP (478 mg, 3.87 mmoles), and THF (100 mL) under nitrogen and then add triethylamine (4.19 g, 41.03 mmoles) and diethylcarbamoyl chloride (5.73 g, 40.99 mmoles). Heat the mixture to reflux and maintain for 6 hours. Cool the reaction to 50° C. Add a mixture of water (20 mL) and acetic acid (0. 67 mL, 11.68 mmoles). Separate the phases and discard the aqueous phase. This yields a solution of diethyl-carbamic acid 2-(4-methoxy-phenyl)-benzo[b]thiophen-6-yl ester in THF.

PREPARATION 2

Diethyl-carbamic acid 3-bromo-2-(4-methoxy-phenyl)-benzo[b]thiophen-6-yl ester Add NBS (7.37 g, 40.99 mmoles) to the solution of diethyl-carbamic acid 2-(4-methoxy-phenyl)-benzo[b]thiophen-6-yl ester in THF at ambient temperature. Stir the mixture for 20 minutes. Distill the resulting solution to 47 mL. Add Methanol (15 mL) to the distilled solution and cool the solution to 50° C. Add seed crystals of Example 2 (340 mg, 0.8 mmoles) to the cooled solution and stir the mixture for 15 minutes. Slowly add water (35 mL). Allow the mixture to cool to ambient temperature, and hold at ambient temperature for one hour. Collect the product by vacuum filtration, wash with aqueous THF (30 mL, 2 water: 1 THF) and dry in a vacuum oven to yield diethyl-carbamic acid 3-bromo-2-(4-methoxy-phenyl)-benzo[b]thiophen-6-yl ester. Yield 15.75 g (36.26 mmol, 93% of theory).

PREPARATION 3

Diethyl-carbamic acid 3-bromo-2-(4-methoxy-phenyl)-1-oxo-1H-1Lambda*4*-benzo[b]thiophen-6-yl ester

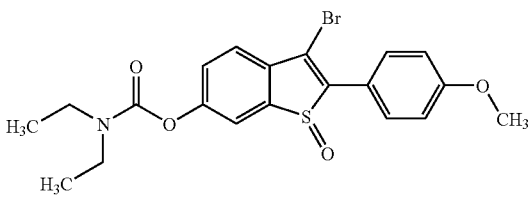

Add diethyl-carbamic acid 3-bromo-2-(4-methoxy-phenyl)-benzo[b]thiophen-6-yl ester (85.0g, 195 8 mmol; limiting reagent) to a solution of sulfolane (510 mL) and sulfuric acid (255 mL, 4783.9 mmol) at −10° C. Add hydrogen peroxide (30%; 20.25 mL; 1.02 eq.) dropwise during a time period of 3 hours, while maintaining the temperature at ~−10° C. Following the end of the addition, stir the mixture for 1 hour, sample, and assay for reaction completion. Once complete, quench any residual oxidant with a 5% aqueous solution of sodium bisulfate (85 mL; 60.4 mmol). Add acetic acid (127.5 mL; 1.5 vol) to the reaction mixture, adjust the temperature to 10° C., and then add water (127.5 mL; 1.5 vol). Adjust the temperature to 20-25° C. Seed the mixture with diethyl-carbamic acid 3-bromo-2-(4-methoxy-phenyl)-1-oxo-1H-1Lambda*4*-benzo[b]thiophen-6-yl ester (2.5 g; 3 wt %) and stir for 2 hours to promote crystal growth. After 2 hours, add water (550 mL; 6.5 vol) over a 3 hour period to complete the crystallization. Stir the slurry for at least 2 hours and filter. Wash the filter cake with water (85 mL; 3 vol), ammonium hydroxide (14%; 85 mL; 3 vol), and water (85 mL; 3 vol).

Dissolve the resultant wet cake at 71° C. in a biphasic solution of ethyl acetate (340 mL; 4 vol) and water (127.5 mL; 1.5 vol). Stir the dissolved product for a minimum of 15 minutes. Then, remove the lower, aqueous layer. Cool the solution to 63-67° C. and seed with diethyl-carbamic acid 3-bromo-2-(4-methoxy-phenyl)-1-oxo-1H-1Lambda*4*-benzo[b]thiophen-6-yl ester (2.5 g; 3 wt %). Ripen the seed for 30-60 minutes and cool the slurry to 0-5° C. over 2-3 hours. Filter the product and wash with cold (0-5° C.) ethyl actetate (85 mL; 1 vol). Dry the product with heat and vacuum at 50-60° C.

PREPARATION 4

Diethyl-carbamic acid 2-(4-methoxy-phenyl)-benzo[b]thiophen-6-yl ester

Charge a vessel with 2-(4-methoxy-phenyl)-benzo[b]thiophen-6-ol (1.000 mol, 256.3 g), 99% DMAP (0.100 mol, 12.34 g), and THF (10.0 L/kg, 2.56 L). Add 99% triethylamine (1.050 mol, 107.3 g) and 97% diethylcarbamyl chloride (DEC-Cl) (1.050 mol, 146.8 g). Heat the contents of the reactor to reflux/66° C. Stir 4 hours or until reaction is complete as determined by HPLC. Begin to cool to 50° C. and add acetic acid solution made up of DI water (3.0 L/kg, 769 mL) and glacial acetic acid (0.300 mol, 18.02 g). Separate the layers at 50° C., and remove the bottom aqueous layer. Cool the organic layer to −5 to 0° C. (−20° C. to ambient is acceptable). The organic layer contains a solution of diethyl-carbamic acid 2-(4-methoxy-phenyl)-benzo[b]thiophen-6-yl ester which is most conveniently carried directly to the next step, the bromination step.

Mass spec (Gradient Positive ESI): found: 356.1307 (M+H), calculated: 356.1320 and found: 378.1122 (M+Na), calculated: 378.1139.

PREPARATION 5

Diethyl-carbamic acid 3-bromo-2-(4-methoxy-phenyl)-benzo[b]thiophen-6-yl ester

To the organic layer containing diethyl-carbamic acid 2-(4-methoxy-phenyl)-benzo[b]thiophen-6-yl ester as described in Example 4, add solid 99% NBS (1.070 mol, 192.4 g). Stir at least 15 minutes and ensure that reaction is complete by HPLC (<0.5% of diethyl-carbamic acid 2-(4-methoxy-phenyl)-benzo[b]thiophen-6-yl ester).

Quench the reaction with a solution of DI water (0.5 L/kg, 128 mL), sodium bicarbonate (0.075 mol, 6.30 g) and 99% sodium thiosulfate pentahydrate (0.050 mol, 12.5 g). Stir for 15 minutes to quench excess NBS and HBr. Reduce the volume to (5.0 L/kg, 1.28 L) by atmospheric distillation. Cool to 55-60° C. and add methanol (2.0 L/kg, 513 mL). Cool to 50° C. Seed w/ 2.0 mol % diethyl-carbamic acid 3-bromo-2-(4-methoxy-phenyl)-benzo[b]thiophen-6-yl ester (0.020 mol, 8.69 g) and stir for approximately 15 minutes. Add DI water over 70 minutes (3.5 L/kg, 897 mL). Cool to 20-25° C. over 1 hour, stir for 1 hour, and filter. Wash with 2:1 water:THF (3.0 L/kg, 769 mL) and dry at 50-80° C./FV.

PREPARATION 6

Diethyl-carbamic acid 3-bromo-2-(4-methoxy-phenyl)-1-oxo-1H-1Lambda*4*-benzo[b]thiophen-6-yl ester Add diethyl-carbamic acid 3-bromo-2-(4-methoxy-phenyl)-benzo[b]thiophen-6-yl ester (85.0 g, 195 8 mmol) to a pre-cooled solution of sulfolane (510 mL) and sulfuric acid (255 mL, 4783.9 mmol) at −10° C. Add hydrogen peroxide (30%; 20.25 mL; 1.02 eq.) dropwise over 3 hours, maintaining the temperature at ~−10° C. Stir the mixture for 1 hour, sample, and assay to determine reaction completion. Once complete, quench any residual oxidant with a 5% aqueous solution of sodium bisulfate (85 mL; 60.4 mmol). Then, to the reaction mixture, add a 50% solution of acetic acid (255 mL; 3.05 vol) and adjust the temperature to 20-25° C. Seed the reaction with diethyl-carbamic acid 3-bromo-2-(4-methoxy-phenyl)-1-oxo-1H-1Lambda*4*-benzo[b]thiophen-6-yl ester (2.5 g; 3 wt %) and stir for 2 hours to promote crystal growth. After 2 hours, add water (550 mL; 6.5 vol) over 3 hours to complete the crystallization. Stir the slurry for at least 2 hours and filter. Wash the filtered cake with water (255 mL; 3 vol), ammonium hydroxide (14%; 255 mL; 3 vol), and water (255 mL; 3 vol) to obtain a wet cake.

Dissolve the resultant wet cake at 71° C. in a biphasic solution of ethyl acetate (340 mL; 4 vol) and water (127.5 mL; 1.5 vol). Stir the dissolved product for a minimum of 15 minutes. Remove the lower, aqueous layer, cool the solution to 63-67° C., and seed with diethyl-carbamic acid 3-bromo-2-(4-methoxy-phenyl)-1-oxo-1H-1Lambda*4*-benzo[b]thiophen-6-yl ester (2.5 g; 3 wt %). After ripening the seed for 30-60 minutes, cool the slurry 0-5° C. over 2-3 hours. Filter the product and wash with cold (0-5° C.) ethyl actetate (85 mL; 1 vol). Dry the product with heat and vacuum at 50-60° C.

EXAMPLE 1

Diethyl-carbamic acid 2-(4-methoxy-phenyl)-1-oxo-3-[4-(2-piperidin-1-yl-ethoxy)-phenoxy]-1H-1Lambda*4*-benzo[b]thiophen-6-yl ester

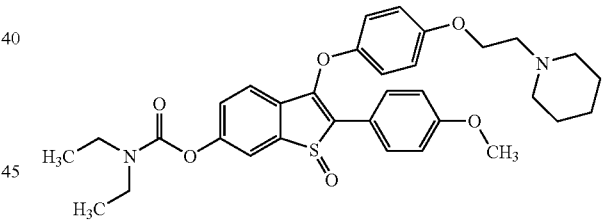

Charge 1.08 eq (1.08 mol, 239.0 grams) of 4-(2-piperidin-1-yl-ethoxy)-phenol to a vessel and then charge 1.03 eq (1.03 mol, 1.03 liter) of a 1 molar solution of potassium t-butoxide in THF to the same vessel. Follow flush charge with a DMF flush of less than 500 mL (volume taken from total DMF charge). Allow the solution to stir for approximately 15 minutes to ensure complete deprotonation of the 4-(2-piperidin-1-yl-ethoxy)-phenol.

Charge 1.0 mol (450.35 g) of diethyl-carbamic acid 3-bromo-2-(4-methoxy-phenyl)-1-oxo-1H-1Lambda*4*-benzo[b]thiophen-6-yl ester to a make-up tank and use not more than 500-1000 mL of DMF to slurry the material for transfer to the reaction vessel (containing the deprotonated 4-(2-piperidin-1-yl-ethoxy)-phenol), and then transfer the batch to the reaction vessel. Use the balance of the DMF to rinse the charge vessel (total DMF charge for initial flush and diethyl-carbamic acid 3-bromo-2-(4-methoxy-phenyl)-1-oxo-1H-1Lambda*4*-benzo[b]thiophen-6-yl ester slurry not to exceed 1.688 liters) into reactor.

Heat reactor to 50° C. and age for 3 hrs at 50° C., or until end of reaction assay shows no more conversion of the diethyl-carbamic acid 3-bromo-2-(4-methoxy-phenyl)-1-oxo-1H-1Lambda*4*-benzo[b]thiophen-6-yl ester to the diethyl-carbamic acid 2-(4-methoxy-phenyl)-1-oxo-3-[4-(2-piperidin-1-yl-ethoxy)-phenoxy]-1H-1Lambda*4*-benzo[b]thiophen-6-yl ester.

In a separate makeup tank, prepare an 8% brine solution with caustic in the following manner by charging with 11.258 liters of water, 900 grams of NaCl, and 67.5 grams of a 50 wt % NaOH solution. Thoroughly mix the solution to ensure complete dissolution of the sodium chloride. To the diethyl-carbamic acid 2-(4-methoxy-phenyl)-1-oxo-3-[4-(2-piperidin-1-yl-ethoxy)-phenoxy]-1H-1Lambda*4*-benzo[b]thiophen-6-yl ester, charge 12.5 L/kg (5.629 liters) of n-butyl alcohol followed by 20% (2.34 liters) of the caustic/brine solution. Agitate for 10 minutes and allow to settle for 10-15 minutes or until two phases have completely separated. Expect a lower aqueous cut of approximately half that of the initial brine/caustic charge. Cut lower aqueous layer keeping rag layer with batch. Repeat the extraction four more times with 20% of the caustic/brine makeup, keeping rag with batch until the fifth and final extraction cut.

Mass spec (Gradient Positive ESI): found: 591.2533 (M+H), calculated: 591.2528.

EXAMPLE 2

Diethyl-carbamic acid 2-(4-methoxy-phenyl)-3-[4-(2-piperidin-1-yl-ethoxy)-phenoxy]-benzo[b]thiophen-6-yl ester

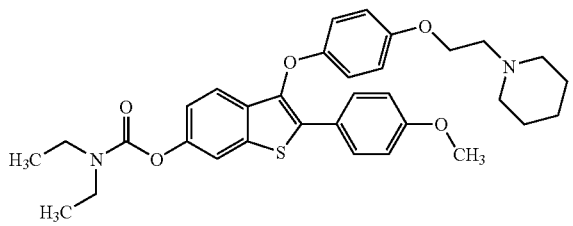

Charge 75% phosphoric acid to the remaining organic layer until the pH is less than 2.0 (expect approximately 340 mL of phosphoric acid solution). Transfer the acidified solution to the hydrogenator and charge the catalyst (0.004 eq, 4.3 grams dry basis) of Johnson Matthey type A501023-10, 10% Pd/C. Follow flush catalyst with 0.5 L/kg DI water (225 mL) directly into hydrogenator. Hydrogenate under 65 PSIG hydrogen pressure at 110° C.

Remove solution containing diethyl-carbamic acid 2-(4-methoxy-phenyl)-3-[4-(2-piperidin-1-yl-ethoxy)-phenoxy]-benzo[b]thiophen-6-yl ester from the hydrogenator and filter the catalyst over filter aid. Rinse the catalyst cake with n-butanol enough to ensure adequate rinsing (as much as 20% of the batch volume is acceptable as a rinse). Charge n-BuOH rinse directly into batch layer.

Mass spec (Gradient Positive ESI): found: 575.2588 (M+H), calculated: 575.2579.

EXAMPLE 3

2-(4-Methoxy-phenyl)-3-[4-(2-piperidin-1-yl-ethoxy)-phenoxy]-benzo[b]thiophen-6-ol or Arzoxifene Free Base Remove the aqueous layer to attenuate the excess phosphoric acid. Then charge 5.0 l/kg of DI water (2251 mL). Adjust pH of the n-butanol solution of diethyl-carbamic acid 2-(4-methoxy-phenyl)-3-[4-(2-piperidin-1-yl-ethoxy)-phenoxy]-benzo[b]thiophen-6-yl ester using KOH pellets to above pH 8.0. Expect approximately 330 grams of 85% KOH. After attaining a pH above 8.0, extract and cut the lower aqueous layer, keeping the rag layer back with the batch.

Charge 5.5 eq (360 grams of 85%) of KOH to the reactor and heat to 108° C. Expect a large volume of distillate to begin coming off at 92.5° C. Once at 108° C., set condenser for total reflux, reduce heat input to maintain temperature, and continue to age at 108° C. until deprotection is complete and less than 0.10% of the diethyl-carbamic acid 2-(4-methoxy-phenyl)-3-[4-(2-piperidin-1-yl-ethoxy)-phenoxy]-benzo[b]thiophen-6-yl ester remains. Sample after 2 hrs to check for completion, then hourly thereafter.

Upon completion of deprotection, cool batch to less than 50° C. and add back n-butanol to 16.5 volumes of solvent (total volume to 7.43 liters). Charge 5.0 l/kg of DI water to the reaction vessel. Settle and cut the lower aqueous layer, keeping rag layer with the batch. Transfer the organic layer to the crystallization vessel with 0.5 volume n-butanol rinse.

Charge 6.6 l/kg DI water to the reactor and heat to 80° C. At temperature, adjust pH to 7.5-8.0 using concentrated HCl. Expect approximately 1.18 eq (105 mL) to reach neutral pH. Correct overshoot using 50 wt % caustic NaOH. Stir for 10 minutes and then settle and cut the lower aqueous layer keeping batch temperature at 85° C. Cut the rag layer forward into waste aqueous layer. Heat the remaining batch to 117° C. and 10 volumes of solvent (4.50 liters). Expect a large volume of distillate beginning at 92.5° C. Charge back fresh n-butanol in 1 volume shots as needed to increase temperature and maintain volume. Once at temperature and volume, cool batch to 40° C. over greater than 2 hours. Confirm the formation of a medium to thick slurry. Reheat batch to 80° C. and age for 30 minutes at 80° C. Confirm survival of the seed material. Slowly cool the batch, over 4 hours, to −5.0° C. Age at −5.0° C. for greater than 2 hours to ensure equilibrium. Filter batch at −5.0° C. and wash the cake with −5.0° C. n-butanol (2 volumes, 900 mL) followed by 2 volumes (900 mL) of −5.0° C. isopropyl alcohol. Dry in vacuo using 60° C. heat until dry.

Mass spec (Gradient Positive ESI): found: 476.1900 (M+H), calculated: 476.1895.

EXAMPLE 4

Preparation of 2-(4-Methoxy-phenyl)-3-[4-(2-piperidin-1-yl-ethoxy)-phenoxy]-benzo[b]thiophen-6-ol Hydrochloride (or Arzoxifene Hydrochloride) Form III Charge 14.3 mL of isopropyl Alcohol, 8.4 mL of DI water, and 10.0 g (21 mmol) of arzoxifene free base. Heat reactor to 50° C. and add 1.12 eq (23.6 mmol, 2.0 mL) of concentrated hydrochloric Acid. Heat to dissolution (~65° C.) and then cool to 58-60° C.

Charge 6.3 mL of DI water and seed the batch with 3.0 wt % (3.0 g) of arzoxifene HCl. Age for 30 minutes.

Charge 56.7 mL of DI water over 4 hours to crystallize the product. Cool to 5-10° C.

Filter and wash the wet cake with 50 mL of a DI water/isopropyl alcohol solution (4:1). Dry in vacuo using 50° C. heat until dry.

X-ray Powder Diffraction of Form III

X-ray powder diffraction analysis is performed with a D8 Diffractometer, equipped with a CuKα source (λ=1.54056 Å) operating at 30 kV and 30 mA. The sample is scanned from 4 to 35 degrees in 2 theta with a step size of 0.007 degrees and a scan time of 0.5 seconds per step. The error for the method is previously established as +/−0.2 degrees. Sample displacement is corrected using Silver Behenate which is a low angle internal standard supplied by Eastman Kodak and characterized by The Gem Dugout of State College, Pa. The sample is analyzed after equilibration in the environmental chamber of the D8 at 30° C. and 35% relative humidity.

| 2 theta angle | Intensity $I/I_0$ |
|---|---|
| 4.54 | 8.1 |
| 7.91 | 100.0 |
| 9.38 | 2.9 |
| 10.26 | 15.0 |
| 10.63 | 1.7 |
| 13.86 | 6.6 |
| 14.07 | 3.9 |
| 15.17 | 6.7 |
| 15.81 | 27.1 |
| 16.41 | 3.8 |
| 17.71 | 62.0 |
| 18.00 | 7.7 |
| 18.18 | 7.7 |
| 20.55 | 20.0 |
| 20.90 | 19.8 |
| 21.35 | 12.6 |
| 21.85 | 1.8 |
| 22.33 | 3.3 |
| 22.90 | 2.7 |
| 23.79 | 21.6 |
| 24.01 | 25.3 |
| 24.41 | 20.1 |
| 27.11 | 4.2 |
| 27.99 | 14.7 |
| 28.77 | 12.4 |
| 30.31 | 4.4 |
| 30.86 | 4.3 |
| 31.54 | 4.6 |
| 33.55 | 0.9 |
| 34.47 | 3.2 |

The x-ray diffraction pattern confirms that the material produced is Form III.

EXAMPLE 5

Alternate Preparation of Diethyl-carbamic acid 2-(4-methoxy-phenyl)-3-[4-(2-piperidin-1-yl-ethoxy)-phenoxy]-benzo[b]thiophen-6-yl ester Dissolve diethyl-carbamic acid 2-(4-methoxy-phenyl)-1-oxo-3-[4-(2-piperidin-1-yl-ethoxy)-phenoxy]-1H-1Lambda*4*-benzo[b]thiophen-6-yl ester (Example 1) (4.0 g, 6.8 mmol) in 80 mL n-propyl alcohol with stirring and then cool the resultant solution to −10° C. Add 37% hydrochloric acid (6.7 g, 67 9 mmol) dropwise at −10° C. within a 10 minute time period. After the mixture is warmed up to ambient temperature, add $Na_2S_2O_3 \cdot 5H_2O$ (6.7 g, 27 0 mmol) and allow the reaction to occur at ambient temperature for 4 hours. Monitor the reaction by $1^1H$ NMR for completion. Carefully add 100 mL of saturated aqueous $NaHCO_3$ to neutralize the reaction mixture and then adjust the pH of the mixture to 7. Add 100 mL $CH_2Cl_2$ and stir. Separate the organic phase, and extract the aqueous phase with $CH_2Cl_2$ (2×50 mL). Wash (with successive washes) the combined organic phase with brine (50 mL) and water (50 mL), dry over anhydrous $Na_2SO_4$, and filter. Remove all the volatiles under reduced pressure, affording 3.4 g of the crude product as a viscous material. Pass this viscous material through a short pad of silica gel with 100% petroleum ether (30-60° C.) and 100% ethyl acetate as the eluents. Collect the ethyl acetate phase and evaporate all the volatiles under reduced pressure, producing 3.2 g of the crude product as a pale yellow viscous material. Add 20 mL of hexane and the mixture is kept at 4° C. overnight, affording the desired product Diethyl-carbamic acid 2-(4-methoxy-phenyl)-3-[4-(2-piperidin-1-yl-ethoxy)-phenoxy]-benzo[b]thiophen-6-yl ester as a white solid (2.9 g, yield 74%, NMR purity>96%) after dried at 40° C./2 mmHg.

EXAMPLE 6

Alternate Preparation of Diethyl-carbamic acid 2-(4-methoxy-phenyl)-3-[4-(2-piperidin-1-yl-ethoxy)-phenoxy]-benzo[b]thiophen-6-yl ester To a 500 mL flask (fitted with a stir bar) add diethyl-carbamic acid 2-(4-methoxy-phenyl)-1-oxo-3-[4-(2-piperidin-1-yl-ethoxy)-phenoxy]-1H-1Lambda*4*-benzo[b]thiophen-6-yl ester (8.46 mmoles; 5.00 g) and methanol (50.00 mL) at ambient temperature. To the resulting yellow slurry, add 36.5% hydrogen chloride (67.71 mmoles; 5.82 mL; 6.76 g) dropwise over 10 minutes to form a yellow solution. Then add solid sodium thiosulfate (25.39 mmoles; 4.06 g). Stir the resulting yellow mixture at 30° C. for 30 minutes and then quench with 100 mL of EtOAc and 200 mL of 0.5 N NaOH. Transfer the mixture to a separation funnel, separate the organic layer, and wash the organic layer with 100 mL of water and 50 mL of brine. Dry over sodium sulfate and concentrate which results in a thick oil. Dissolve the thick oil into 20 mL of t-butyl methyl ether (MTBE) and then add 50 mL of heptane. Stir the white slurry at room temperature overnight. Collect the white solid by filtration and wash with 50 mL of heptane. Dry in a vacuum oven at 50° C. for 5 hours and obtain 3.6 g of diethyl-carbamic acid 2-(4-methoxy-phenyl)-3-[4-(2-piperidin-1-yl-ethoxy)-phenoxy]-benzo[b]thiophen-6-yl ester as a white solid. MS: [M+H]: 575.2.

Preparation of 2-(4-Methoxy-phenyl)-3-[4-(2-piperidin-1-yl-ethoxy)-phenoxy]-benzo[b]thiophen-6-ol Hydrochloride (or Arzoxifene Hydrochloride) Form V One Molar Description Charge 2.00 l/kg (951 mL) of methyl alcohol and 0.35 l/kg (166 mL) of water to a suitably sized reactor. Charge 1.10 eq conc. HCl (98.5 mL) to reactor and heat contents to 50° C. Charge 1.0 eq (1.000 mol, 475.6 g) of arzoxifene freebase to reactor. Immediately the solids will likely fully dissolve. Heat contents of the reactor to near reflux (68° C.-70° C.) and verify full dissolution of the solids. Filter the solution.

Charge pre-seed MeOH (2.50 l/kg, 1190 mL) to reactor and cool contents of the reactor to 60° C. At temperature (60° C.), seed reactor with 3.0 wt % (14.3 grams) pure arzoxifene HCl, form V. Allow seed to age for 30 minutes.

Cool the reactor contents using the following profile: cool to 52° C. over 1 hour, then cool to 40° C. over 1 hour, and finally cool to −5° C. over at least 2 hours. Stir for at least an hour at −5° C. Filter the slurry and wash the cake with pre-chilled (−5° C.) MeOH (2 l/kg, 951 mL). Dry at 55° C. in vacuo until dry.

X-ray Powder Diffraction of Form V

X-ray powder diffraction analysis is performed with a Bruker D4 Diffractometer, equipped with a CuKα source (λ=1.54056 Å) operating at 50 kV and 40 mA. The sample is scanned from 4 to 35 degrees in 2-theta with a step size of 0.009 degrees and a scan time of 0.5 seconds per step. The error for the method is previously established as +/−0.2 degrees. Sample displacement is corrected using Silver Behenate which is a low angle internal standard supplied by Eastman Kodak and characterized by The Gem Dugout of State College, Pa.

| 2-theta angle | Intensity I/I$_0$ (%) |
|---|---|
| 7.28 | 100 |
| 8.97 | 20.2 |
| 9.94 | 9.6 |
| 12.85 | 30.9 |
| 14.57 | 26.2 |
| 15.51 | 75.9 |
| 15.88 | 53.5 |
| 17.56 | 55.7 |
| 18.00 | 58.8 |
| 18.23 | 53.1 |
| 19.00 | 76.9 |
| 19.85 | 24.6 |
| 21.43 | 45.2 |
| 21.55 | 57.2 |
| 22.59 | 23.3 |
| 23.27 | 20.8 |
| 24.35 | 36.6 |
| 25.78 | 36.2 |
| 27.39 | 30.3 |
| 28.17 | 21.5 |
| 30.11 | 15.4 |
| 30.69 | 9.7 |
| 32.20 | 12.7 |

We claim:

1. A compound of the formula:

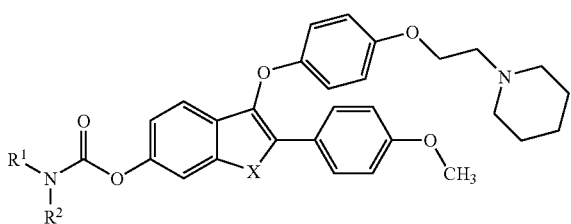

wherein
X is S or S(O);
$R^1$ and $R^2$ are each independently selected from the group consisting of —CH$_2$CH$_3$ and phenyl; or $R^1$ and $R^2$ combine to form morpholino.

2. A compound of claim 1 wherein X is S.

3. A compound of claim 1 wherein X is S(O).

4. A compound as claimed by any claim 1 wherein $R^1$ and $R^2$ are each —CH$_2$CH$_3$.

5. A compound that is diethyl-carbamic acid 2-(4-methoxy-phenyl)-3-[4-(2-piperidin-1-yl-ethoxy)-phenoxy]-benzo[b]thiophen-6-yl ester.

6. A process for preparing arzoxifene comprising:
a) reducing an intermediate sulfoxide compound of the formula:

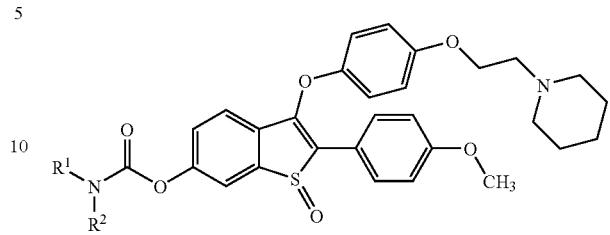

to form a compound of the formula:

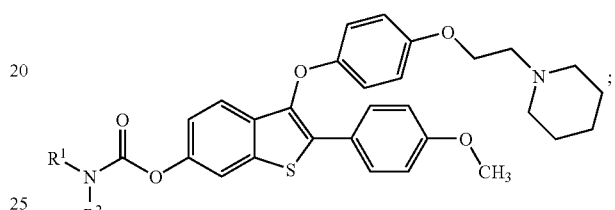

wherein $R^1$ and $R^2$ are each independently selected from the group consisting of —CH$_2$CH$_3$ and phenyl; or $R^1$ and $R^2$ combine to form morpholino; and
b) deprotecting the sulfide compound to form arzoxifene.

7. A process of claim 6 wherein arzoxifene is prepared as the free base.

8. A process of claim 6 further comprising salinating arzoxifene to form the hydrochloride salt.

9. A process of claim 6 further comprising preparing arzoxifene as Form III arzoxifene.

10. A process of claim 6 further comprising preparing arzoxifene as Form V arzoxifene.

11. A process as claimed by claim 6 wherein the intermediate sulfoxide compound is reduced using Na$_2$S$_2$O$_3$.

12. A process as claimed by claim 11 wherein the intermediate sulfoxide compound is reduced using Na$_2$S$_2$O$_3$/HCl.

13. A process as claimed by any claim 6 wherein the intermediate sulfoxide compound is reduced using H$_2$.

14. A process as claimed by claim 6 wherein the intermediate sulfoxide compound is reduced using Pd on carbon as a catalyst.

15. A process as claimed by claim 6 wherein the deprotection comprises isopropanol washes.

16. A process as claimed by claim 6 wherein $R^1$ and $R^2$ are each —CH$_2$CH$_3$.

* * * * *